United States Patent [19]

Shell et al.

[11] 4,303,637

[45] Dec. 1, 1981

[54] MEDICATION INDICATED FOR OCULAR HYPERTENSION

[75] Inventors: John W. Shell, Hillsborough; Robert M. Gale, Mountain View, both of Calif.

[73] Assignee: ALZA Corporation, Palo Alto, Calif.

[21] Appl. No.: 137,456

[22] Filed: Apr. 4, 1980

[51] Int. Cl.$^3$ .......................... A61K 9/22; A61K 9/26; A61K 9/50
[52] U.S. Cl. ..................................... 424/14; 128/260; 424/19; 424/22; 424/28
[58] Field of Search .............. 128/260; 424/14, 19–22, 424/28

[56] References Cited

U.S. PATENT DOCUMENTS

| | | | |
|---|---|---|---|
| 3,933,998 | 1/1976 | Seidehamel et al. | 424/28 |
| 4,179,497 | 12/1979 | Cohen et al. | 424/22 |
| 4,186,184 | 1/1980 | Zaffaroni | 424/14 |

*Primary Examiner*—Shep K. Rose
*Attorney, Agent, or Firm*—Paul L. Sabatine; Edward L. Mandell

[57] ABSTRACT

An ocular therapeutic system is disclosed for dispensing a medicament to an ocular environment. The system comprises a beta-blocking drug in a polymer with the drug surrounded by the polymer. A method is disclosed for the management of ocular hypertension using the system. Also disclosed, is a composition comprising the drug and the polymer.

24 Claims, 3 Drawing Figures

MEDICATION INDICATED FOR OCULAR HYPERTENSION

FIELD OF THE INVENTION

This invention relates to ocular pharmacology. More particularly, the invention pertains to (1) a noval and useful ocular therapeutic system housing a beta-adrenergic blocking osmotically effective solute, and to (2) a method for the management of intraocular pressure by dispensing the drug solute from the system to an eye. Also, the invention concerns a composition of matter comprising the solute and the polymer, which composition is useful for manufacturing a dispensing system.

DESCRIPTION OF THE PRIOR ART

Recently, a beta-blocking drug, timolol, was introduced to ocular pharmacology in solution form as an useful drug for the management of intraocular pressure. This drug is administered to the eye as liquid eyedrops for lowering intraocular pressure associated with glaucoma, as described by Zimmerman et al, in *Invest. Ophthalmol. Visual Sci.*, Vol. 16, pages 623 to 624, 1977; and by Wettrell et al, in *Brit. J. of Ophthal.*, Vol 61, pages 334 to 338, 1977.

While, the eyedrop method of administration is suitable in a few instances, serious limitations are associated with its use. For example, eyedrops exhibit a relatively brief residence time in the eye, necessitating frequent reapplication, usually 1 to 4 times daily, and sometimes more frequently. Another limitation of the eyedrop is volumetric. The normal volume to which the ocular tear film can increase is limited before it overflows, and the action of eye-blinking reduces this volume; yet, the conventional dropper delivers drops that exceed this volume. Thus, the familiar act of instilling eyedrops is complicated, as the reflux blinking that accompanies this act results in a loss of administered drug from the tear film, and consequent removal of drug from contact with the eye. These limitations impose an uncertainty on the quantity of drug delivered and they force the therapist to seek an improved form of therapy; see Wright et al., *Arch. Ophthalmol.*, Vol. 67, pages 564 to 565, 1962; and Mishima et al., *Ophthalmol.*, Vol. 5, pages 264 to 276, 1966.

In the light of the above presentation, it is evident a critical and heretobefore unsatisfied need existed for a dosage form for administering beta-blocking drugs to the eye substantially-free from the tribulations associated with the prior art dosage forms. The beta-blocking drugs however, possess properties which contraindicate their manufacture into other dosage forms, including ocular therapeutic systems. For example, these drugs, particularly those having a phenyl group, an aliphatic alcohol, and an alkyl substitution on a nitrogen atom, are unstable in the presence of light and air, and subject to discoloration an oxidation. These properties would preclude from their manufacture into an ocular system, which is subsequently placed in an eye, because the eye is rich with both light and air. *The Extra Pharmacopoeia*, by Martindale, Twenty-seventh Edition, pages 1312, 1320 to 1321, 1324, 1327 to 1328, 1977.

Also, these drugs possess amine moieties which can cause the drug to function as a plasticizer when dispersed in a polymer. The introduction of a drug that can act as a plasticizer molecule primarily affects the glass transition of a polymer used to make the system. That is, plasticization of the system by the drug can lower its glass transition temperature by reducing interchain forces, leading to an unpredictable and unknown rate of release of the drug from the system. *Textbook Of Polymer Science*, by Billmeyer, page 220, 1962, published by Interscience Publishers, New York.

It will be appreciated by those versed in the ocular and medical arts, that if a system can be provided that dispenses beta-blocking drugs for the management of intraocular pressure without the limitations of the prior art, such a system would have a definite use and represent a substantial contribution to the art. Likewise, it will be further appreciated by those versed in the art, that if an ocular therapeutic system is made available for delivering these drugs for the management of glaucoma, such a system would have a positive value and represent an unexpected advancement in the field of ocular pharmacology.

OBJECTS OF THE INVENTION

Accordingly, it is an immediate object of the invention to provide a novel and useful ocular therapeutic system that can deliver certain beta-blocking drugs substantially-free of the tribulations associated with the prior art.

Another object of the present invention is to provide an ocular therapeutic system that can dispense selected beta-blocking drugs that are useful for the management of intraocular pressure.

Another object of the invention is to provide an ocular therapeutic system for dispensing a beta-blocking solute at a controlled rate for use as an anti-glaucoma medication.

Yet another object of the invention is to provide an ocular insert that embraces an osmotic structure, houses a beta-blocking drug solute, and releases the solute at an osmotically controlled rate.

Still another object of the invention is to provide a method indicated for the management of ocular hypertension by using an ocular insert that delivers a beta-blocking drug solute to an ocular environment for the management of said hypertension.

Another object of the invention is to provide a composition of matter comprising a polymer and a beta-blocking drug which composition is useful for manufacturing drug delivery systems.

Another object of the invention is to provide an ocular device than can administer a beta-blocker with a diminished incidence of side effects previously associated with the prior art for of drop administration.

These objects, as well as other objects, features and advantages of the invention will become more readily apparent from the following detailed description, the drawings and the accompanying claims.

SUMMARY OF THE INVENTION

This invention concerns an ocular therapeutic system manufactured as an insert useful for the management of glaucoma. The insert houses and dispenses a therapeutic beta-blocking drug solute at a controlled and beneficial rate over a prolonged period of time. The invention also pertains to a method of using the insert for dispensing the therapeutic solute for treating glaucoma. The invention further relates to a polymer beta-blocking solute composition useful for making the insert.

BRIEF DESCRIPTION OF THE DRAWINGS

In the drawings, which are not drawn to scale, but are set forth to illustrate embodiments of the invention, the Figures are as follows.

In the drawings and specification, like parts in related Figures are identified by like numbers. The terms appearing earlier in the specification and in the description of the drawings as well as embodiments thereof, are further described elsewhere in the disclosure.

DETAILED DESCRIPTION OF THE DRAWINGS

Figure 1:
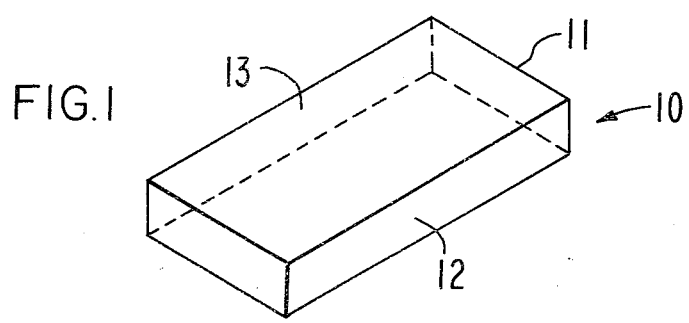
FIG. 1 is a view of an ocular therapeutic system made and used according to the mode and manner of the invention.

Turning now to the drawings in detail, which are an example of an ocular insert for dispensing a beta-adrenergic blocking drug, and which examples are not to be construed as limiting, one insert is indicated in FIG. 1 by the numeral 10. System 10, as seen in FIG. 1 is enlarged for illustration, is an ocular therapeutic system manufactured for administering a beta-blocking drug to an ocular environment, particularly the eye of a warm-blooded animal, preferably a human. System 10 comprises a body 11 made of a film consisting essentially of a single, solid polymer 12, and it, 10, has at least one surface 13 for releasing a previously selected beta-blocking drug to the eye.

System 10 is manufactured as an insert or drug delivery device, sized, shaped, structured and adapted for easy insertion and comfortable retention in the eye. The system can have any geometric shape, and its dimensions can vary conductive with good ocular therapy. The lower limit on the size of system 10 is governed by the amount of drug to be housed and administered to elicit the desired pharmacologic response, as well as the smallest sized system that can be conveniently inserted and maintained in the eye. The upper limit on the size of system 10 is governed by the space limitations of the eye, consistent with comfortable insertion and retention in the eye. Satisfactory results can be obtained with ocular systems having a length of 2 to 20 millimeters, a width of 1 to 20 millimeters, and a thickness of 0.1 to 7.5 millimeters. The system can be inserted in the upper, or the lower cul-de-sac of the eye of a human for prolonged, comfortable retention and therapy. Ocular system 10 is made of non-toxic, flexible bioacceptable materials that are non-allergenic to the eye, and it, 10, is designed for the eye of animals in need thereof, particularly mammals and humans.

System 10 comprises the selected beta-blocking drug solute dispensed as a plurality of discrete depots, not shown, through a polymer matrix 12. The polymer surrounds and embraces the beta-blocking solute, and binds them into a solid, unit body 11. Polymer 12 surrounds the depots individually so that each depot is encapsulated by a layer of polymer 12. Polymer 12 is made from a matrial that is non-toxic, substantially non-erodible and non-dissolvable in the eye and in eye fluid, is substantially impermeable to the passage of the drug solute, and it is permeable to the passage of an external fluid, that is tear fluid. The beta-blocking drug is present as an osmotically effective solute for dispensing it from the insert over time.

In operation, when system 10 is in a fluid environment of use, the fluid diffuses into polymer 12 and is imbibed into the depots of the drug solute dissolving the drug therein. The rate of fluid imbibition into each depot is related to the osmotic pressure gradient exhibited by the drug solute across the polymer encapsulating the depot against the external fluid. As fluid is imbibed into a depot, it continuously dissolves the drug solute and continuously fills the depot, which drug solute solution thereby generates a hydrostatic pressure in the depot. This pressure is applied against the polymer causing it to rupture and form an aperture. Drug is then released through the aperture from the ruptured depot near the surface of insert 10 to the eye. The drug is continuously released from insert 10 by the inward progressive formation of apertures in depots forming lattice drug connected dispensing paths in polymer 12 for releasing drug from within insert 10 to its exterior. The dispensing paths can form openings on all sides of system 10, and they can be interconnected through tortuous paths of regular and irregular shapes discernible by microscopic examination. As eye fluid is imbibed into a depot, it fills the paths and it becomes a means for enhancing drug transport therethrough, with release occuring at a controlled and continuous rate over a prolonged period of time.

Figure 2:
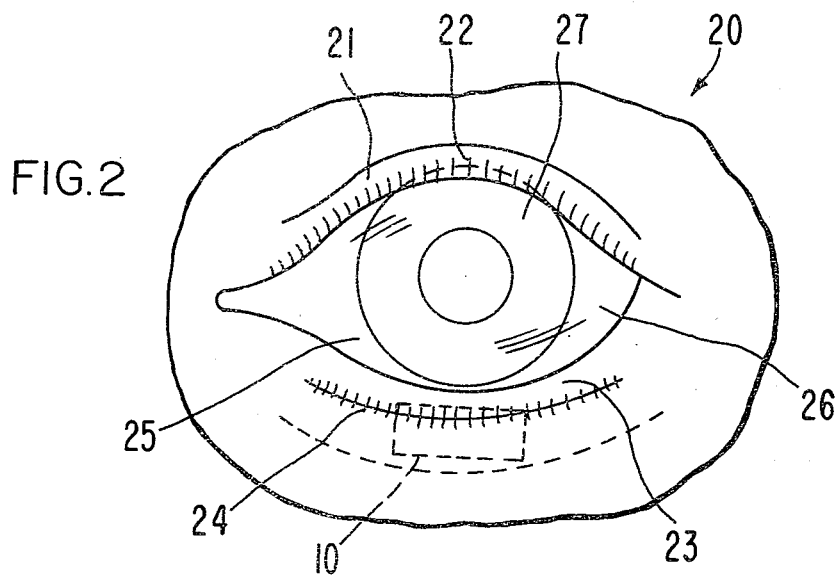
FIG. 2 is an illustration of the system of FIG. 1 depicting the system in operation dispensing a drug solute to an ocular environment; and, FIG. 3 is a graph dipicting the release rate profile for a system made according to the invention.

Referring to FIG. 2, ocular therapeutic system 10 is shown in an eye for administering a beta-blocking drug to eye 20. Eye 20 comprises an upper eyelid 21 with eyelashes 22 at the edge of eyelid 21, and a lower eyelid 23 with eyelashes 24 at the edge of eyelid 23. Eye 20 anatomically comprises an eyeball 25 covered for the greater part of its posterior area by sclera 26 and its central area by cornea 27. Eyelids 21 and 23 are lined with an epithelial membrane or palpebral conjunctiva, not seen in FIG. 2, and sclera 26 is lined with a bulbar conjunctiva, not shown in FIG. 2. The portion of the palpebral conjunctiva that lines the lower eyelid 23 and the underlying portion of the bulbar conjunctiva defines a lower cul-de-sac. System 10 may be shaped, sized and adapted for insertion and retention in any area of the eye, and of the presently preferred embodiments, system 10 is sized, shaped and adapted for insertion in the lower cul-de-sac. In FIG. 2, system 10 is seen in broken continuous lines in the lower cul-de-sac, generally held in position by the normal pressure of the eyelid.

DETAILED DESCRIPTION OF THE INVENTION

In accordance with the practice of this invention, and in light of the above presentation, it has now been suprisingly found this invention can provide an ocular therapeutic system for dispensing a beta-blocking drug at a controlled rate and in a therapeutically effective amount over a prolonged period of time. The system dispenses the drug to an eye in an effective amount for the management of ocular hypertension over time.

The phrase beta-receptor blocking drug as used for the purpose of this invention denotes a beta-receptor blocking drug solute that exhibits an osmotic pressure gradient across the polymer wall forming a depot against an external fluid. The phrase includes beta-adrenergic blocking drug, beta-adrenoceptor blocking drug, and more simply beta-blockers that competitively inhibit the agonistic action of catecholamines at adrenergic beta-receptor sites. The drugs are useful for treating glaucoma and lowering ocular hypertension.

The beta-receptors exists as two types, termed $beta_1$, and $beta_2$. The former mediate cardiac stimulation, the latter relaxation of vascular and bronchial smooth muscles. Drugs which block both $beta_1$ and $beta_2$ receptors are termed non-selective, those that block $beta_1$ blockers are termed $beta_1$ blockers, and drugs that are selective and block $beta_2$ receptors only are called $beta_2$ blocking drugs.

The beta-blocking osmotically effective solutes useful for the purpose of this invention are bioactive solutes that occupy and interact with a biomolecular receptor. The drugs comprise a ring moiety possessing aromatic properties, and it is covalently bonded through a carbon atom of the armoatic ring to an aliphatic alcoholamine. The ring embraces a monocyclic, carbocyclic character, and it can be unsubstituted or substituted. The solutes are, in a presently preferred embodiment, the non-toxic salts, such as the corresponding pharmaceutically acceptable acid addition salts thereof.

More specifically, the beta-blocking solutes useful for the present purpose comprise a solute of the formula selected from the group consisting of (1) $R_1$—O—$CH_2$—$CH(OR_2)$—$CH_2$—NH—$R_3$, and (2) $R_5$—$CH(OR_2)$—$CH(R_4)$—NH—$R_3$, wherein:

$R_1$ is a member selected from the group consisting essentially of unsubstituted and substituted phenyl, indanyl, and indenyl, with the substituent bonded thereto a member selected from the group consisting essentially of lower alkyl, lower alkenyl, lower alkynyl, lower alkyloxy, lower alkenyloxy, lower alkynyloxy, lower alkoxy-lower alkyl, lower alkoxy-lower alkoxy, lower alkythio, lower alkenylthio, lower alkylthio-lower alkyl, lower alkoxy-lower alkylthio, halogen, halogen-lower alkyl, hydroxyl, hydroxyl-lower alkyl, carboxyl, carbamoyl, N-lower alkyl carbamoyl, N,N-di-lower alkyl carbamoyl, N-lower alkyl carbamoyl-lower alkyl, N,N-di-lower alkyl carbamoyl-lower alkyl, acyl, acyloxy, acylamino, lower alkanoylamino-lower alkyl, lower alkanoylamino-lower alkyl, lower alkanoylaminolower alkenyl, lower alkanoylamino-lower alkynyl, lower alkanoylamino-lower alkoxy, N-lower alkylamino, N,N-di-lower alkylamino, lower alkoxycarbonyl, lower alkoxycarbonylamino, lower alkoxycarbonylamino-lower alkyl, lower alkoxycarbonylamino-lower alkenyl, lower alkoxycarbonylamino-lower alkoxy, lower alkylcarbonylamino-lower alkyl, N'-lower alkyl-ureido, N', N'-di-lower alkyl-ureido, lower alkylsulphonylamino, cyano, nitro, and, cycloaliphatic;

$R_2$ is a member selected from group consisting of hydrogen and acyl;

$R_3$ is a member selected from the group consisting of lower alkyl, lowr alkenyl, lower alkynyl, cycloaliphatic, aryl, araliphatic, lower alkyl-aryl, lower alkoxy-aryl, lower alkyl aryl-lower alkoxy, lower alkyl aryl-lower alkyl, lower alkyl aryl-lower akenyl, lower alkyl aryl-lower alkynyl, lower alkoxy aryl-lower alkyl, lower alkoxy aryl-lower alkenyl, lower alkoxy aryl-lower alkynyl, lower alkoxy and aryl-lower alkoxy, aryl-lower alkyl, aryl-lower alkenyl, aryl-lower alkynyl, aryl-lower alkoxy, aryloxy-lower alkyl, aryloxy-lower alkoxy, N-lower alkylcarbamoyl, N,N-di-lower alkylcarbamoyl, lower alkoxycarbamoyl-lower alkyl, cyano-lower alkyl, aryl-carbamoyl, and lower alkoxyphenyl-carbamoyl;

$R_4$ is a member selected from the group consisting of hydrogen and lower alkyl;

$R_5$ is the same as $R_1$ with the proviso that when $R_5$ is substituted with a hydroxyl group, the aromatic ring has covalently bonded thereto and additional ring substituent other than hydroxyl and its selected from the $R^1$ group of substituents; and wherein the beta-blocker is present as an osmotic solute, preferrably as the pharmaceutically acceptable salt.

The term alkyl as used herein denotes both straight and branched chain alkyl groups of 1 to 7 carbon atoms inclusive, such as methyl, ethyl, n-propyl, iso-propyl, n-butyl, iso-butyl, test-butyl, pentyl, iso-pentyl, neopentyl, n-hexyl, iso-hexyl, n-heptyl, and the like.

The term lower alkenyl denotes straight and branched chain alkenyl groups of 2 to 7 carbon atoms, such as 3,3-dimethylallyl, 1-isobutenyl, 2-methyl-1-butenyl, 2-methyl-2-pentenyl, and the like.

The term lower alkynyl includes straight or branched chain alkynyl groups of 2 to 7 carbons, such as ethynyl, 2-propynyl, 2-butynyl, 1-propynyl, 2-penten-4-ynyl, and the like.

The term lower alkyloxy or lower alkoxy denotes straight or branched chain alkoxy groups of 1 to 7 carbon atoms, for example methoxy, ethoxy, propoxy, butoxy, n-pentoxy, n-hexoxy, isopropoxy, 2-butoxy, isobutoxy, 3-pentoxy, and the like.

The term lower alkenyloxy denotes straight and branched chain lower alkenyloxy groups and the positional isomers thereof, having 2 to 7 carbons, for example ethenoxy, propenoxy, butenoxy, penteoxy, hexenoxy iso-propenoxy, iso-butenoxy, sec-butenoxy, 2-methyl-1-butenoxy, 2,3-dimethyl-1-butenoxy, and the like.

The term lower alkynyloxy embraces straight and branched chain alkynyloxy groups of 2 to 7 carbon atoms, such as ethynyloxy, 2-propynyloxy, 3-butynyloxy, 3-pentynyloxy, and the like.

The term lower alkoxy-lower alkyl embraces methoxymethyl, ethoxymethyl, isopropyethyl, and the like. The term lower alkoxy-lower alkoxy embraces for example, methoxymethoxy, methoxyethoxy, ethoxyethoxy, ethoxyisopropoxy, and the like. The term hydroxyl-lower alkyl is, for example, hydroxymethyl, 1- or 2-hydroxyethyl, and the like.

The term lower alkylthio is for example, methylthio, ethylthio, isopropylthio, n-butylthio, and the like. The term lower alkenythio is illustrated by 1-propenylthio, 1-butenythio, 3-pentenylthio, and the like. Lower alkylthio-lower alkyl is illustrated by methylthiomethyl, ethylthioethyl, 2-methylthiomethyl, 2-ethylthioethyl, and the like. Lower alkoxy-lower alkylthio is illustrated by methoxymethylthio, ethoxymethylthio, and the like.

The term halogen is depicted by chlorine, bromine, fluorine, and iodine. The term halogen-lower alkyl is exemplified by trifluoromethyl, trichloromethyl, and the like.

The terms N-lower alkyl-carbamoyl and N,N-di-lower alkylcarbamoyl are for example, N-methyl-carbamoyl, N-ethyl-carbamoyl, N,N-dimethyl-carbamoyl, N,N-diethylcarbamoyl, N,N-ethylpropylcarbamoyl, and the like. The terms N-lower alkyl-carbamoyl-lower alkyl, and N,N-di-lower alkylcarbamoyl-lower alkyl are illustrated by N-methylcarbamoylmethyl, N,N-diethylcarbamoylethyl, and the like.

The term acyl embraces acyl groups having from 1 to 18 carbon atmos inclusive, such as alkaoyl, alkenoyl, aroyl, substituted derivatives thereof, and the like. Typical alkanoyl groups include formyl, acetyl, propionyl, isobutyryl, valeryl, isovaleryl, pivaloyl, lauroyl, palmitoyl, stearoyl, isomeric forms thereof, and the like. Typical alkenoyl groups include acryloxyl, methacryloyl, crotonoyl, isocrotonyl, elaidoyl, 3-butenoyl, β-methyl-α- butenoyl, and the like. Typical aroyl groups include benzoyl, toluoyl, hydratropyl, phenylacetyl, cinnamoyl, p-ethoxybenzoyl, allyloxyphenylacetyl, p-alloxybenxoyl, and the like.

The term acyloxy embraces alkanoyloxy, alkenoyloxy, and aryloxy, where the acyl is as defined, and further illustrated by acetyloxy, propionyloxy, pivaloyloxy, acryloyloxy, benzoxyloxy, and the like. The terms acylamino embraces alkanoylamino and alkenylamino, with the acyl as defined, and the nitrogen atom a bridge between the acyl, a ring, an aliphatic chain, or other points of covalent attachment. Exemplary acylamino are formylamino, acetylamino, propionylamino, pivaloylamino, and the like.

The terms lower alkanoylamino-lower alkyl, lower alkanoylamino-lower alkenyl, lower alkanoylamino-lower alkynyl, and lower alkanoylamino-lower alkoxy denote an alkanoyl of 1 to 8 carbons, preferably with nitrogen and a linking oxygen separated from each other, for example, 2-acetylaminoethoxy, 2-propionylaminoethoxy, 2-pivaloylaminoethoxy, 2-pivaloylaminoethyl, 2-acetylamino-ethyl, 2-propionylaminoethyl, and the like.

The terms N-lower alkylamino and N,N-di-lower alkylamino are illustrated by methylamino, ethylamino, propylamino, n-butylamino, diethylamino, dimethylamino, methylethylamino, and the like.

The terms lower alkoxycarbonyl, lower alkoxycarbonylamino, lower alkoxy carbonylamino-lower alkyl, lower alkoxycarbonylamino-lower alkenyl, lower alkoxycarbonylamino-lower alkoxy, and lower alkylcarbonyl amino-lower alkyl, are represented by methoxycarbonylaminoethyl, methoxycarbonyl, ethoxycarbonylaminoethyl, methoxycarbonylaminopropyl, 2-ethoxycarbonylaminoethyl, tert-butoxycarbonylaminoethyl, ethyl-carbonylamino, methylcarbonylaminoethyl, ethoxycarbonyl, and the like.

The terms N'-lower alkyl-ureido, and N',N'-di-lower alkyl-ureido are exemplified by N'-methylureido, N'-ethylureido, N',N'-dimethylureido, N',N'-diethylureido, and the like.

Lower alkylsulphonylamino is illustrated by methylsulphonylamino, ethylsulphonylamino, propylsulphonylamino, and the like.

The term cycloaliphatic includes cycloalkyl rings of 3 to 6 carbon atoms such as cyclopropyl, cyclobutyl, cyclopentyl, cyclohexyl, and the like.

The term aromatic as used herein denotes a ring that resembles benzene in behavior. The ring may possess aromatic properties and have a total structure that differs from the structure of benzene; however, there is a similarity in electronic configuration or electronic behavior. The term aryl denotes phenyl, benzyl, indanyl, indenyl and the like. The term aralipathic denotes an aromatic ring covalently bonded to an aliphatic moiety exemplified by lower alkyl, lower alkoxy, lower alkenyl and the like.

The terms lower-aryl, lower aryl-lower alkoxy, lower alkyl aryl-lower alkyl, lower alkyl aryl-lower alkenyl, lower alkyl aryl-lower alkynyl, lower alkoxy aryl-lower alkyl, lower alkoxy aryl-lower alkenyl, lower alkoxy aryl-lower alkynyl, lower alknoxy aryl-lower alkoxy, aryl-lower alkyl, aryl-lower alkenyl, aryl-lower alkynyl, aryl-lower alkoxy, aryloxy-lower alkyl, aryloxy-lower alkoxy are illustrated by methylphenyhl, allylphenyl, ethynylphenyl, 2-cyclopropylphenyl, 2-hydroxymethylphenyl, methoxymethyl-phenyl, carbamoylmethylphenyl, methoxyphenyl, allyloxyphenyl, phenylethyl, methallylloxyphenyl, 2-chloro-5-methyl-phenyl, and the like. The terms cyano-lower alkyl, arylcarbamoyl, lower alkoxy-phenylcarbamoyl are illustrated by cyanomethyl, cyanomethylphenyl, carbamoylphenyl, 2-(4-carbomoylphenoxy)-methyl, and the like.

The phrase beta-blocking osmotically effective solute as used for the present purpose denotes a solute that exhibits an osmotic pressure gradient across the polymer wall forming the depot of the system against an exterior fluid. The phrase includes therapeutically acceptable salts, such as the inorganic acid addition salts including borate, hydrobromide, hydrochloride, nitrite, hydroiodide, nitrate, phosphate, sulfamate, sulfate, and the like. The organic acid addition salts include the acetate, ascorbate, 2-acetoxybenzoate, 2-phenylbenzoate, benzoate, bitartrate, cinnamate, citrate, embonate, fumurate, glycollate, hydroxymalate, malate, maleate, methylmaleate, mandelate, nicotinate, isonicotinate, oxalate, propionate, salicylate, succinate, 4-aminosalicylate, methanesulphonate, benzenesulphonate, tartarate, tannate, and the like.

Beta-receptor blocking osmotically effective solute drugs embraced by the above formulae for the purpose of this invention are exemplified by the following beneficial drugs. The drugs which contain centers of asymmetry can be used in the form of mixtures of isomers, as the racemates, in the form of pure isomers, and in the form of optically active antipodes. Exemplary drugs are acebutolol or N-[3-acetyl-4[2-hydroxy-3-[(1-methylethyl)amino]propoxy[-phenyl]butanamide; alprenolol or 1-[(1-methylethyl)amino[-3-[2-(2-propenyl)-phenoxy]-2-propanol; atenolol or 1-p-carbamoylmethyl-phenoxy-3-isopropylamino-2-propanol; bevantol or 1-[3,4-dimethoxyphenethyl)amino-3-(m-tolyloxy)-2-propanol; bupranolol or 1-(tert-butylamino)-3-[(6-chloro-m-tolyl)oxy]-2-propanol; bunitrolol or 2-[3-[1,1-dimethyl)amino]-2-hydroxy-propoxy]benzonitrile; butoxamine or erythro-1-(2,5-dimethoxyphenyl)-2-(tert-butylamino)-propanol; exaprolol or 1-(o-cyclohexylphenoxy)-3-(isopropylamino)-2-propanol; indenolol or 1-[1-H-inden-4-yloxy]-3-[1-methylethylamino]-2-propanol; indanolol or 1-[indan-4-yloxy]-3-[1-methylethylamino]-2-propanol; labetalol or 5-[1-hydroxy-2-[(1-methyl-3-phenylpropyl)amino]ethyl]salicylamide; metoprolol or (±)-1-(isopropylamino)-3-[p-(β-methoxyethyl)phenoxy]-2-propanol; morprolol or 1-(2-methoxyphenoxy)-3-[(1-methylethyl) amino]-2-propanol; nifenalol or 1-(4-nitrophenyl)-2-isopropylamino)ethanol; nitrolol or 1-(4-nitrophenyl)-2-(isopropylamino)propanol; oxprenolol or 1-(isopropylamino)-2-hydroxy-3-[o-(allyloxy)-phenoxy]propane; pamatolol or methyl-(±)-[p-[2-hydroxy]-3-isopropylamino)propoxy]phenylethyl]-carbamate; penbutolol or 1-(2-cyclopentylphenoxy)-3-[(1,1-dimethyl ethyl)amino]-2-propanol; pargolol or 1-[1,1-dimethylethyl)amino-3-[2-(2-propynyloxy)-phenoxy]-2-propanol; procinolol or 1-(2-cyclopropylphenoxy)-3-[(1-methylethyl)amino]-2-propanol; practolol or 1-(4-actamidophenoxy)-3-isopropylamino-2-propanol; sotalol or N-[4-[1-hydroxy-2[(1-methylethyl)amino]ethyl]phenylmethane sulfonamide; tiprenolol or 1-[(1-methylethyl)-amino]-3-[2-(methaylthio)-phenoxy]-2-propanol; tolamolol or 4-[2-[[2-hydroxy-3-(2-methoxy-phenoxy)propoxy]amino]-ethoxy]-benzamide; and, toliprolol or 1-(isopropylamino)-3-(m-totyloxy)-2- propanol. The beta-blocker solutes are known to the art in *The Merck Index*, Ninth Edition, pages 19, 310, 884, 1488, 1516, 6019, 6063, 6763, 7234, 7506, 7584, 7628, 9170 and 9219, 1976; in *Unlisted Drugs*, Vol. 23, No. 9, page 127, 1971; ibid, Vol. 24, No. 5, page 66, 1972; ibid, Vol. 25, No. 8, page 132, 1973; ibid, Vol. 25, No. 9, page 141, 1973; ibid, Vol. 27, No. 8, page 127, 1975; ibid, Vol. 28, No. 7, page 116, 1976; ibid, Vol. 29, No. 1, pages 17, 1977; ibid, Vol. 29, No. 7, page 112, 1977; ibid, Vol. 29, No. 12, page 194, 1977; ibid, Vol. 30, No. 6, page 96, 1978; ibid, Vol. 31, No. 2, page 25, 1979; ibid, Vol. 31, No. 6, page 88, 1979; *USAN and USP Dictionary of Drug Names*, pages 61, 178, 208, 231, 235, 289, 302, 313, 314, 1978; *Ann. Rept. In Med. Chem.*, Vol. 10, pages 51 to 60, 1975; and ibid, Vol. 14, pages 81 to 90, 1979.

Materials suitable for manufacturing system 10 can be selected from naturally occurring and synthetic polymeric materials. These materials are biologically compatible with an animal body, particularly in eye, the form body 11 of system 10, and they are the encapsulating layer that forms the depot surrounding the beta-blocker solute. The materials used are substantially impermeable to the passage of solute, they are permeable to the passage of biological fluid and water, and they form depot apertures during operation of system 10 in the environment of use.

Exemplary materials for forming system 10 housing the beta-blocker solute include a member selected from the group consisting of poly(olefins), poly(vinyl-olefins), poly (styrene), poly(halo-olefins), poly(vinyls), poly(acrylate), poly(methacrylate), poly(oxides), poly(esters), poly(amides), poly(carbonates), the homopolymers, copolymers, straight, branched-chain, and cross-linked derivatives thereof.

More exemplary materials for fabricating system 10 include ethylene-vinyl ester copolymers having an ester content of 4 to 80% such as ethylene-vinyl acetate copolymer, ethylene-vinyl hexanoate copolymer, ethylene-vinyl butyrate copolymer, ethylene-vinyl pentanatoate copolymer, ethylene-vinyl trimethyl acetate copolymer, ethylene-vinyl diethyl acetate copolymer, ethylene-vinyl 3-methyl butanoate copolymer, ethylene-vinyl-3,3-dimethyl butanoate copolymer, and ethylene-vinylbenzoate copolymers, acrylonitrile-methyl vinyl ether copolymer, vinyl chloride-diethylfumarate copolymers, homopolymers and copolymers of partially hydrolyzed poly(vinyl alcohol), plasticized poly(amides), poly(isoprene), poly(ethylene), poly(propylene), lightly crossed-link poly(vinyl pyrrolidone), ethylene-propylene copolymers, poly(urethanes), poly(tetrafluoroethylene), and the like. The polymers useful for the purpose of the invention have a molecular weight of about $11 \times 10^4$ to $5 \times 10^6$. The ethylene-vinyl ester copolymrs used for the manufacture of diffusional drug delivery devices wherein the drug dissolves in and passes through the copolymer by the process of diffusion is the invention of Higuchi and Hussain as disclosed and claimed in U.S. Pat. No. 4,144,317 and assigned to the ALZA Corporation of Palo, Alto, California. Solutes, as used for the present purpose in salt and/or ionic states do not dissolve in and diffuse through polymers, as reported in *Biological Science, Molecules to Man*, by Welch et al, pages 157 and 158, published by Houghton Mifflin Company, Boston. The polymeric materials that are used herein generally are non-biodegradable, are non-dissolvable, permeable to the passage of fluid, impermeable to the passage of drug solute and preferably have a low modulus of elasticity. The polymers are known in *Handbook of Common Polymers*, by Scott, et al., Sections 1 through 42, 1971, published by CRC Press, Cleveland, Ohio; and in *Encyclopedia of Polymer Science and Technology*, Edited by Bikales, N. M., Vol. 1 through 17, 1965, published by Wiley Inc., New York.

System 10 houses from about 0.01 weight percent to 50 weight percent of beta-blocker drug solute with the remaining weight percent, up to 100 weight percent polymer. Generally, the system comprises 2 to 50 weight percent, with a presently preferred range of 5 to 40 weight percent solute. Generally, the beta-blocker solute will have a particle size of about 0.1 to 400 microns, a preferred particle size of 0.5 to 100 microns, and a presently preferred particle size of 0.5 to 50 microns. The devices of this invention release about 1 nanogram to 500 micrograms per hour, preferrably 1 microgram to 100 micrograms per hour, and a presently preferred rate of release of 1 microgram to 50 micrograms per hour. The device can release over a prolonged period of time of from 1 hour to 30 days, and more preferably from 4 hours to 14 days.

Procedures for ascertaining the permeability and the impermeability of polymeric films are known to the art in *Proc. Roy. Sci. London*, Series A, Vol. 148, 1935; *J. Pharm. Sci.*, Vol. 55, pages 1224 to 1229, 1966; and in *Diffusion in Solids, Liquids and Gases*, by Jost, Chapter XI, pages 436, to 488, 1960, published by Academic Press, Inc. NY.

Procedures for measuring aperture formation resulting in dispensing system 10 by the hydrostatic pressure in a depot exceeding the cohesive integrity of the polymer, with the polymer opening for releasing a beta-blocker solute to the environment of use, can be determined by measurements predicated on pressure-deflection and mechanical behavior measurements techniques reported in *Modern Plastics*, Vol. 14, pages 143 to 144, 146 and 182, 1964; *Handbook of Common Polymers*, by Scott et al., pages 588 to 609, 1971; *Machine Design*, pages 107 to 111, 1975; *J. Sci. Instruments*, Vol. 42, pages 591, to 596, 1965; and by measuring mechanical stress-strain patterns of polymers using the Instron ® Test Machine, available from Instron Corporation, Canton, Massachusetts.

The osmotic pressure, ATM, of the solute can be measured in a commercially available osmometer that measures the vapor pressure difference between pure water and a solution containing a solute to be analyzed, and according to standard thermodynamic principles, the vapor pressure ratio is converted into an osmotic pressure. An osmometer that can be used for the present measurements is the Model 302B, Vapor Pressure Osmometer, manufactured by the Hewlett Packark Company, Avondale, Pennsylvania.

Procedures for measuring the surface area average diameter of solutes are reported in *J. Am. Chem. Soc.*, vol. 60, 309, 1938; *The Surface Chemistry of Solids*, by Gregg, Second Edition, 1961, published by Reinhold Corporation, New York; *Adsorption, Surface Area and Porosity*, by Gregg, et al., 1967 published by Adademic Press, New York; *Physical Adsorption of Gases*, by Yound et al., 1962, published by Butterworth and Company, Ltd., London; and, *Fine Particle Measurements*, by Valla, 1959, published by Macmillan, New York.

The ocular systems are manufactured by first micronizing a beta-blocking drug solute, then admixing this solute with a polymer to form a composition. The composition is next heated and processed on a roller mill, or it is processed in an internal mixing bowl to form a predevice comprising polymer surrounding an encapsulating drug solute. The encapsulated solute then is cast as a film, or extruded as a film and cut into ocular inserts, or it is injection molded into inserts, ready for releasing the drug to an eye for the management of ocular hypertension. General manufacture procedures are disclosed by Michaels and Gulloid in U.S. Pat. No. 4,177,256.

DETAILED DESCRIPTION OF THE INVENTION

The following examples are illustrative of the present invention and they should not be considered as limiting the scope of the invention in any way, as these examples and equivalents thereof will become more apparent to those versed in the art in the light of the present disclosure, the drawings, and the accompanying claims.

EXAMPLE 1

Figure 3:
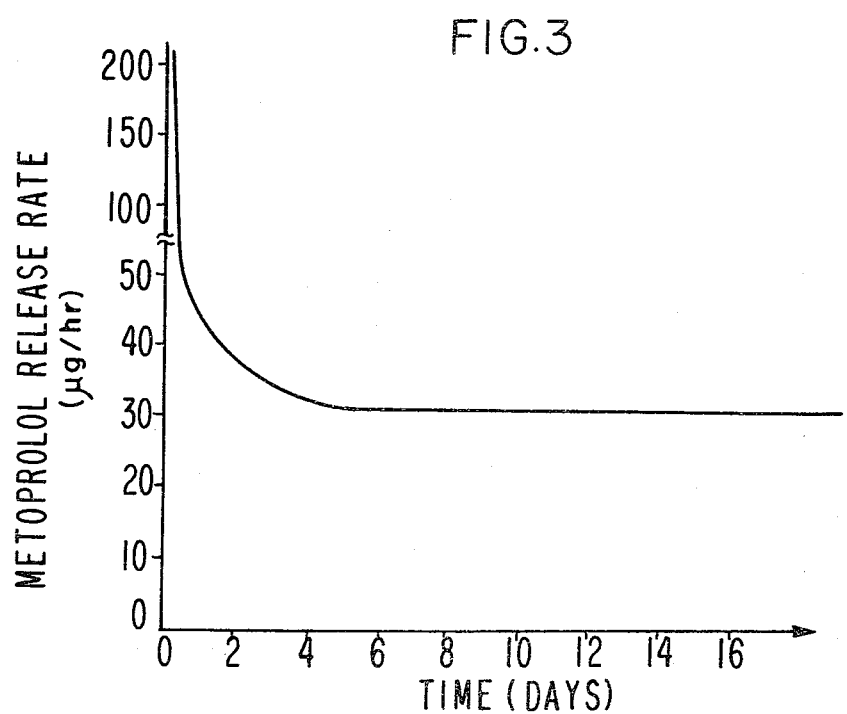

An ocular medication dispensing system 10 comprising depots housing the beta-blocker solute, $(\pm)$-1-(isopropylamino)-3-[p-($\beta$methoxyethyl)phenoxy]-2-propanol fumarate, metoprolol fumarate, was manufactured by first micronizing separately the solute and then blending them with a polymer. The procedure comprises placing 65 grams of ethylene-vinyl acetate copolymer onto a conventional rubber mill and milled until banded on the rollers. Then 35 grams of the metroprolol fumarate were added slowly over a period of several hours during which time the drug was worked into the copolymer. The drug polymer composition was removed from the two roll mill and passed between the rolls after folding it several times. This process was repeated many times to insure a uniform dispersion of the drug in the copolymer. The drug copolymer composition was then comminuted in a grinder to reduce it to sections measuring about 2 mm in diameter. These sections then were fed to an injection molder, Arlburg, affixed with a die-mold. The mixture was then injection molded at 80° C. and 400 psi into elliptical ocular inserts 14×6×1.2 mm, Moninal. The drug release rate profile of the systems was determined by shaking them in a normal saline media at 37° C. At frequent intervals the release media was completely changed and the procedure repeated for additional measurements. The drug concentrations in the media were ascertained by UV and converting the values to drug release rates. After a transient initially high release rate, these inserts released drug at about 30 microgram an hour, as the base, for greater than 12 days. These results are presented in FIG. 3. The results, when extrapolated indicate the systems would have a release duration of about one month. On macroscopic examination, the system appeared substantially free from photolysis and oxidation.

EXAMPLE 2

An ocular, osmotic, medicating dispensing system of elliptical shape and comprised of depots housing 1-(tert-butylamino)-3-[(6-chloro-m-tolyl)oxy]-2-propanol hydrochloride is manufactured by first micronizing the drug, and blending it into a homogeneous composition. Next, the drug is encapsulated as depots by slowly adding the composition over a period of 7 to 15 minutes, with continuous milling, to a heated two-roll mill previously charged with copolymeric ethylene-ethyl acrylate. The depot forming procedure is repeated by re-milling an appropriate number of times, with the depot in the copolymer removed from the mill, an then extruded into a film. Next, the film is die-cut to yield systems for releasing the drug to an ocular environment over time.

EXAMPLE 3

An ocular insert for releasing 1-(2-acetyl-4-n-butyramidophenoxy)-2-hydroxy-3-isopropylaminopropane hydrochloride to the eye of an animal is prepared as follows: 75 parts of a commercially available poly(olefin), poly(ethylene) and 25 parts of the above solute of 35 micron size are compounded on a Brabender Plastograph ® with gentle heat for 7 to 14 minutes until the solutes are surrounded with poly(ethylene). The mass is removed from the machine and pressed at 15,000 psi into a film having a thickness of 2 mm. Then, rectangle-shaped inserts, 14×6 mm, are die-cut from the film to yield a product useful for the management of ocular hypertension. The solute encapsulated by the polymer is protected from direct exposure to air and light for enhancing the physical and chemical integrity of the solutes.

EXAMPLE 4

An ocular insert manufactured for placement and releasing $(\pm)$-1-[4-(2-methoxyethyl)-phenoxy]-3-[(1-methylethyl)amino]-2-propanol tartrate having a solubility of 860 mg/ml in distilled water at 25° C., an osmotic pressure of 210 atm, a drug particle size of 30 micron average, and a molecular weight of 417.47, of the ocular receptive drug to the eye of a warm blooded animal is prepared as follows: 70 parts of a commercially available polymer, ethylene-vinyl acetate-acrylic acid terpolymer consisting of 28% vinyl acetate, 1% acrylic acid, and the balance of ethylene is compounded on a Barbender Plastograph ® with gentle heating for 10 to 15 minutes until the solute is individually surrounded by the terpolymer. The product is removed from the internal mixer and passed through the cooled rolls of a 3×8 inch roller mill to form a 0.8 mm thick film, with portions of the film compression molded between heated plattens of a hydraulic press to form 0.4 mm thick film. The film is cooled, and elliptical ocular shaped devices are punched from the dry film. The therapeutic solute housed in a plurality of depots on macroscopic examination will evidence resistance to photodegradation and oxidation.

EXAMPLE 5

To 65 grams of ethylene-vinyl acetate copolymer having a vinyl acetate content of 28% in a Barbender Plastograph ® internal mixing bowl, equipped with roller blades, which copolymer is masticated for 2 to 4 minutes, is added [1-(isopropylamino)-2-hydroxy-3-[o-allyloxyphenoxy]propane hydrochloride, having a molecular weight of 301.84, a crystal melting point of 107° to 109° C., and a particle size of 40±10 micron size, and the osmotic, insert forming members blended for 20 minutes at 40 rpm. Next, the contents of the bowl are removed, cut into 3 mm ×3 mm pieces with a multi-blade strip die, and the strips fed to the hopper of an extruder. The strips have a residence time of 5 minutes in the extruder with the screw of the extruder rotating at 20 rpm. A film is extruded through a 12 mil opening at the end of the extruder, and then punched with a stainless steel punch into 13.5×5.8 mm inserts. The ocular inserts release a therapeutically amount of drug for the management of ocular hypertension over time.

EXAMPLE 6

First, 72 grams of ehtylene-vinyl acetate copolymer having a vinyl acetate content of 28% and a molecular weight of 200,000 is added to a Banbury mixing bowl mounted on a Barbender preparation center, and the copolymer allowed to masticate for five minutes, during this time the temperature rises to 60° C. Next a pre-weighed amount of 28 grams of 1-(o-cyclohexylphenoxy)-3-(isopropylamino)-2-propanol sulfate salt; is slowly added to the mixing bowl. After all the drug solute is added to the internal mixing bowl, the solute is encapsulated as depots by the copolymer over 15 minutes. Then, the contents of the bowl are removed and cut into small pieces and fed into the hopper of an extruder. The precut insert is extruded through the debuteuse at the end of the extruder into a 0.7 mm thick film, at 75° C. Next, elliptical shaped monolithic inserts are cut from the film, having dimensions of 14×6 mm. These inserts release the drug expressed as the free base over prolonged period of up to 14 days. The inserts will exhibit a substantially zero order rate of release into a 0.9% saline sink at 37° C., measured spectrophometrically.

The systems of the invention can be used for the management of intraocular pressure associated with glaucoma. The systems are useful for treating primary glaucoma including narrow-angle acute, and wide-angle or chronic simple glaucoma, secondary glaucoma, and preoperatively in acute-angle closure where a delay of surgery is desired in order to lower intra-ocular tension. Glaucoma and its biological effects in human, are described in *The Pharmacological Bases of Therapeutics*, by Goodman and Gilman, 4th Edition, pages 458 to 460, 1970, published by the Macmillian Company, New York, and in *General Ophthalmology*, by Vaughn and Asbury, pages 192 to 209, 1974, published by Lange Medical Publications, Los Altos, California.

While specific considerations, examples and disclosures have been described and discussed herein, such have been offered solely to exemplify the present invention, and they should not be considered as limiting the scope of the nature of the invention.

We claim:

1. An ocular insert comprising depots of from 0.01 weight percent to 50 weight percent of a beta-adrenergic receptor blocker drug solute comprising a solute of the formula selected from the group consisting of (1) $R_1$-O-$CH_2$-$CH$-$(OR_2)$-$CH_2$-NH-$R_3$ and (2) $R_5$-$CH(OR_2)$-$CH(R_4)$-NH-$R_3$ wherein:

$R_1$ is a member selected from the group consisting essentially of unsubstituted and substituted phenyl, indanyl and indenyl, with the substituent bonded thereto a member selected from the group consisting essentially of lower alkyl, lower alkenyl, lower alkynyl, lower alkyloxy, lower alkenyloxy, lower alkynyloxy, lower alkoxy-lower alkyl, lower alkoxy-lower alkoxy, lower alkylthio, lower alkenylthio, lower alkylthio-lower alkyl, lower alkoxy-lower alkylthio, halogen, halogen-lower alkyl, hydroxyl, hydroxyl-lower alkyl, carboxyl, carboamoyl, N-lower alkyl carbamoyl, N,N-dilower alkyl carbamoyl, N-lower alkyl carbamoyl-lower alkyl, N,N-di-lower alkyl carbamoyl-lower alkyl, lower alkanoylamino-lower alkenyl, lower alkanoylamino-lower alkenyl, lower alkyanoylamino-lower alkenyl, lower alkoxy, N-lower alkylamino, N,N-di-lower alkylamino, lower alkoxycarbonyl, lower alkoxy-carbonylamino, lower alkoxycarbonylamino-lower alkyl, lower alkoxycarbonylamino-lower alkenyl, lower alkoxycarbonylamino-lower alkoxy, lower akylcarbonylamino-lower alkyl, N'-lower alkyl-ureido, N,N'-di-lower alkyl-ureido, lower alkylsulphonylamino, cyano, nitro, and, cycloaliphatic;

$R_2$ is a member selected from the group consisting of hydrogen and acyl;

$R_3$ is a member selected from the group consisting of lower alkyl, lower alkenyl, lower alkynyl, cycloaliphatic, aryl, araliphatic, lower alkyl-aryl, lower alkoxy-aryl, lower alkyl aryl-lower alkoxy, lower alkyl aryl-lower alkyl, lower alkyl aryl-lower alkenyl, lower alkyl aryl-lower alkynyl, lower alkoxy aryl-lower alkyl, lower alkoxy aryl-lower alkenyl, lower alkoxy aryl-lower alkynyl, lower alkoxy aryl-lower alkoxy, aryl-lower alkyl, aryl-lower alkenyl, aryl-lower alkynyl,aryl-lower alkoxy, aryloxy-lower alkyl, aryloxy-lower alkoxy, N-lower alkylcarbamoyl, N,N-di-lower alkylcarbamoyl, lower alkoxycarbamoyl-lower alkyl, cyano-lower alkyl, arylcarbamoyl, and lower alkoxyphenyl-carbamoyl;

$R_4$ is a member selected from the group consisting of hydrogen and lower alkyl;

$R_5$ is the same as $R_1$ with the provisions when $R_5$ is substituent with hydroxyl, the ring has an additional substituent other than hydroxyl bonded thereto selected from $R_1$; and the remaining weight percent up to 100 weight percent of a pharmaceutically acceptable, non-toxic polymer, that surrounds substantially individually the depots of the beta-adrenergic drug solute, and binds them into the ocular insert, said polymer a member selected from the group consisting of poly(olefin), poly(vinylolefin), poly(halo-olefin), poly(styrene), poly(vinyl), poly(acrylate), poly(methacrylate), poly(oxide), poly(ester), poly(amide), and poly(carbonate), which insert is sized, shaped and adapted for easy insertion and prolonged retention in the eye for administering a therapeutically effective amount of the drug thereto to occupy and interact with the beta-receptors for managing intraocular pressure over a prolonged period of time.

2. The ocular insert to claim 1 wherein the polymer is non-biodegradable, permeable to the passage of fluid, and substantially impermeable to the passage of drug solute.

3. The ocular insert according to claim 1 wherein the polymer has a molecular weight of from $1 \times 10^4$ to $5 \times 10^6$.

4. The ocular insert according to claim 1 wherein the drug solute has a particle size of from 0.1 to 400 microns.

5. The ocular insert according to claim 1 wherein the solute is the pharmaceutically acceptable non-toxic salt and it is a member selected from the group consisting of inorganic an organic acid addition salts.

6. The composition of matter consisting essentially of from 0.01 weight percent of 50 weight percent of a beta-adrenergic receptor blocker drug solute selected from the group consisting of acebutolol, alprenolol, atenolol, bevantol, bupranolol, bunitrolol, exaprolol, indenolol, indanolol, labetalol, metoprolol, moprolol, nifenalol, nitrolol, oxprenolol, pamatolol, penbutolol, pargolol, procinolol, practolol, sotalol, triprenolol, tolamolol, and toliprolol, said drug solute present as the therapeutically acceptable salt in the composition with up to 100 weight percent of a polymer that is non-toxic, non-biodegradable and non-dissolvable when in contact with aqueous and biological fluids, said polymer a member selected from the group consisting of poly(olefin), poly(vinyl-olefin), poly(halo-olefin), poly(styrene), poly(vinyl), poly(acrylate), poly(methacrylate), poly(oxide), poly(ester), poly(amide), and poly(carbonate), and which composition forms a film sized, shaped and adapted for easy insertion and prolonged retention in a biological environment of use for releasing a therapeutically effective amount of the beta-adrenergic receptor blocker drug to the biological environment over a prolonged period of time.

7. The composition of matter according to claim 6 wherein the polymer has a molecular weight of from $1 \times 10^4$ to $5 \times 10^6$.

8. The composition of matter according to claim 6 wherein the drug solute salt has a particle size of 0.1 to 400 microns.

9. The composition of matter according to claim 6 wherein the polymer is permeable to aqueous and biological fluid and substantially impermeable to the passage of beta-adrenergic receptor blocker drug solute.

10. The composition of matter according to claim 6 wherein the beta-adrenergic receptor blocker drug solute exhibits an osmotic pressure gradient across the polymer when it is a film.

11. An ocular therapeutic insert for the dispensing of a beta-adrenergic receptor blocker drug to an eye, said system sized, shaped and structured for easy insertion and adapted for comfortable retention in the eye, and comprising depots of from 0.01 weight percent to 50 weight percent of the drug solute selected from the group consisting of acebutolol, alprenolol, atenolol, bevantol, bupranolol, bunitrolol, exaprolol, indenolol, indanolol, labetalol, metoprolol, moprolol, nifenalol, nitrolol, oxprenolol, pamatolol, penbutolol, pargolol, procinolol, practolol, sotalol, triprenolol, tolamolol and toliprolol, said drug solute present as the therapeutically acceptable salt of 0.1 to 400 micron size, said depots dispersed in and surrounded substantially individually by up to 100 weight percent of polymer that is non-toxic, non-biodegradable, substantially impermeable to the passage of drug solute, is permeable to the passage of eye fluid, and which polymer is a member selected from the group consisting of poly(olefins), poly(vinyl-olefins), poly(acrylates), poly(methacrylates), poly(oxides), poly(esters), poly(amides) and poly(carbonates).

12. The ocular therapeutic insert for dispensing the beta-adrenergic receptor blocker drug according to claim 11, wherein the drug solute is present as the therapeutically acceptable addition salt, selected from the group consisting of inorganic acid addition salts, organic acid addition salts, and quaternary addition salts.

13. The ocular therapeutic insert for dispensing the beta-adrenergic receptor blocker drug according to claim 11, wherein the drug solute is a salt that exhibits an osmotic pressure gradient across the polymer wall forming the depot against an exterior fluid and is a member selected from the group consisting of borate, hydrobromide, hydrochloride, hydroiodide, nitrate, nitrite, phosphate, sulfamate, sulfate, acetate, ascorbate, benzoate, bitartrate, cinnamate, citrate, embonate, fumurate, glycollate, malate, maleate, mandelate, nicotinate, oxlate, propionate, salicylate, succinate, tartarate, and tannate.

14. An ocular insert consisting essentially of (a) discrete depots of a medication osmotically effective solute selected from the group consisting of acebutolol, alprenolol, atenolol, bevantol, bupranolol, bunitrolol, exaprolol, indenolol, labetalol, metoprolol, moprolol, nifenalol, nitrolol, oxprenolol, pamatolol, penbutolol, pargolol, procinolol, practolol, sotalol, triprenolol, tolamolol and toliprolol, which solutes have a size of 0.1 to 100 microns and exhibit an osmotic pressure gradient across the wall of the depot against an external fluid present in the environment of use; (b) a film of a member selected from the group consisting of poly(olefin), poly(vinyl-olefin), poly (halo-olefins), poly(styrene), poly(vinyls), poly(acrylates), poly(methacrylate), poly(oxide), poly(esters), poly(amide), and poly(carbonate), forming the insert, imparting size and shape to the insert for easy insertion and prolonged retention in the environment of use, said film substantially impermeable to the passage of solute, permeable to the passage of the external fluid, nondissolvable in the fluid, and substantially surrounds individually and serves as the wall of the depots; and (c) wherein when the insert is positioned in the environment of use, fluid from the environment is imbibed through the wall into the depots to continuously dissolve the solutes and generate a hydrostatic pressure in the depots, which pressure is applied against the wall of the depots thereby forming apertures and releasing the medication from the depots at the surface and from within the insert by the inward progressive aperature formulation in depots at a controlled rate over a prolonged period of time.

15. In a method for treating glaucoma in a warm-blooded animal, which method consists essentially in lowering the intraocular pressure associated with glaucoma by administering to the eye of the animal a medication, for glaucoma, the method consisting essentially in the steps of:

(a) positioning in the eye an ocular insert containing said medication, the improvement wherein said insert comprises:

(1) discrete depots of ocular administrable medication of the formula $R_1-O-CH_2-CH(OR_2)-CH_2-NH-R_3$ wherein: $R_1$ is a member selected from the group consisting essentially of unsubstituted and substituted phenyl, indanyl and indenyl, with the substitutent bonded thereto a member selected from the group consisting essentially of lower alkyl, lower alkenyl, lower alkynyl, lower alkyloxy, lower alkenyloxy, lower alkynyloxy, lower alkoxy-lower alkyl, lower alkoxy-lower alkoxy, lower alkylthio, lower alkenylthio, lower alkylthio-lower alkyl, lower alkoxy-lower alkylthio, halogen, halogen-lower alkyl, carboxyl, carbamoyl, N-lower alkyl carbamoyl, N,N-di-lower alkyl carbamoyl, N-lower alkyl carbamoyl-lower alkyl, N,N-di-lower alkyl carbamoyl-lower alkyl, acyl, acyloxy, acylamino, lower alkanoylamino-lower alkenyl, lower alkanoylamino-lower alkynyl, lower alkanoylamino-lower alkoxy, N-lower alkylamino, N,N-di-lower alkylamino, lower alkoxycarbonyl, lower alkoxycarbonylamino, lower alkoxycarbonylamino-lower alkyl, lower alkoxycarbonylamino -lower alkenyl, lower alkoxcarbonylamino-lower alkoxy, lower alkylcarbonylamino-lower alkyl, N'-lower alkyl-ureido, N',N'-di-lower alkyl-ureido, lower alkylsulphonylamino, cyano, nitro and cycloaliphatic; $R_2$ is a member selected from the group consisting of hydrogen and acyl; and $R_3$ is a member selected from the group consisting of lower alkyl, lower alkenyl, lower alkynyl, cycloaliphatic, aryl, araliphatic, lower alkylaryl-lower alkenyl, lower alkyl aryl-lower alkynyl, lower alkoxy aryl-lower alkyl, lower alkoxy aryl-lower alkynyl, lower alkoxy aryl-lower alkoxy, aryl-lower alkyl, aryl-lower alkenyl, aryl-lower alkyl, aryl-lower alkenyl, aryl-lower alkynyl, aryl-lower alkoxy, aryloxy-lower alkyl, aryloxy-lower alkoxy, N-lower alkyl, aryloxy-lower alkoxy, N-lower alkylcarbamoyl, N,N-di-lowere alkylcarbamoyl, lower alkoxycarbamoyl-lower alkyl, cyano-lower alkyl, aryl-carbamoyl and lower alkoxyphenylcarbamoyl; which solutes exhibit osmotic pressure gradients across the wall of the depot against an external fluid, said depots dispersed in;

(2) a film sized and shaped as an insert for easy positioning and comfortable retention in the eye of the animal, said film an ocular acceptable polymeric material that surrounds individually and forms the wall of the discret depots, is nonerodible, impermeable to the passage of the solutes, and permeable to the passage of fluid;

(b) imbibing fluid from the eye into the depots to dissolve the solutes and fill the depots with solution, thereby exerting pressure against the wall of the depot and forming apertures that release formulation from the depots at the surface and from the interior of the insert through beta-adrenergic receptor blocking medication paths by the inward progressive aperture formation in closely related depots; thereby (c) dispensing the medication embraced by the formula at a controlled rate for treating glaucoma over a prolonged period of time.

16. The method for treating glaucoma in an animal according to claim 15 wherein the animal is a human, the polymeric material is nondissolvable in eye fluid, and the paths formed by inward progressive aperture formation are filled with eye fluid containing the medication.

17. The method for treating glaucoma in an animal according to claim 15 wherein the animal is a human, the medication is metoprolol and the polymeric material is ethylene-vinyl acetate copolymer.

18. The method for treating glaucoma in an animal according to claim 15 wherein the animal is a human, the medication is oxprenolol, and the polymeric material is ethylene-vinyl acetate copolymer.

19. The method for treating glaucoma in an animal according to claim 15 wherein the glaucoma is wide-angle glaucoma.

20. The method for treating glaucoma in an animal according to claim 15 wherein the glaucoma is secondary glaucoma.

21. The ocular therapeutic insert for dispensing the beta-adrenergic receptor drug to the eye according to claim 11, wherein the poly(olefin) is ethylene-vinyl acetate copolymer.

22. The ocular therapeutic insert for dispensing the beta-adrenergic receptor blocker drug to the eye according to claim 11, wherein the poly(olefin) is ethylene-vinyl acetate copolymer, and the drug is metoprol.

23. The ocular therapeutic insert for dispensing the beta-adrenergic receptor blocker drug the eye according to claim 11, wherein the poly(olefin) is ethylene-vinyl acetate copolymer, and the drug is oxprenolol.

24. The ocular insert according to claim 1 wherein the beta-adrenergic receptor blocking drug solute is ($\pm$)-1-(isopropylamino)-3-[p-($\beta$-methoxyethyl)phenoxy]-2-propanol.

* * * * *